(12) United States Patent
Uchiyama et al.

(10) Patent No.: US 11,634,373 B2
(45) Date of Patent: Apr. 25, 2023

(54) BISPHENOL COMPOSITION AND METHOD FOR PRODUCING SAME, AND POLYCARBONATE RESIN AND METHOD FOR PRODUCING SAME

(71) Applicant: MITSUBISHI CHEMICAL CORPORATION, Chiyoda-ku (JP)

(72) Inventors: Kei Uchiyama, Chiyoda-ku (JP); Kazuhisa Hatakeyama, Chiyoda-ku (JP); Makoto Nakamura, Chiyoda-ku (JP); Toshio Uchibori, Chiyoda-ku (JP); Michitaka Ise, Chiyoda-ku (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 16/797,124

(22) Filed: Feb. 21, 2020

(65) Prior Publication Data

US 2020/0190003 A1 Jun. 18, 2020

Related U.S. Application Data

(63) Continuation of application No. PCT/JP2018/031023, filed on Aug. 22, 2018.

(30) Foreign Application Priority Data

Aug. 22, 2017 (JP) .............................. JP2017-159687
Dec. 6, 2017 (JP) .............................. JP2017-234313

(51) Int. Cl.
| | | |
|---|---|---|
| *C07C 37/20* | (2006.01) | |
| *C07C 39/16* | (2006.01) | |
| *C08G 64/20* | (2006.01) | |
| *C07C 37/68* | (2006.01) | |
| *B01J 27/053* | (2006.01) | |
| *C08G 64/06* | (2006.01) | |

(52) U.S. Cl.
CPC ........... *C07C 37/685* (2013.01); *B01J 27/053* (2013.01); *C07C 37/20* (2013.01); *C07C 39/16* (2013.01); *C08G 64/06* (2013.01); *C08G 64/20* (2013.01); *C07C 2527/053* (2013.01)

(58) Field of Classification Search
None
See application file for complete search history.

(56) References Cited

U.S. PATENT DOCUMENTS

| | | | | |
|---|---|---|---|---|
| 5,278,279 A | * | 1/1994 | Kanno ................. | C08G 63/64 524/117 |
| 6,284,931 B1 | | 9/2001 | Isota et al. | |
| 6,653,513 B1 | | 11/2003 | Iwahara | |
| 2010/0121018 A1 | | 5/2010 | Yoshida et al. | |
| 2019/0055180 A1 | | 2/2019 | Nishida et al. | |
| 2021/0070727 A1 | * | 3/2021 | Echigo ...................... | C08G 8/00 |

FOREIGN PATENT DOCUMENTS

| | | | |
|---|---|---|---|
| CN | 101679623 A | | 3/2010 |
| CN | 104591972 A | * | 5/2015 |
| JP | 62-138443 A | | 6/1987 |
| JP | 07-112949 A | | 5/1995 |
| JP | H09-124530 A | | 5/1997 |
| JP | 09-278697 A | | 10/1997 |
| JP | 2000-026349 A | | 1/2000 |
| JP | 2000-128817 A | | 5/2000 |
| JP | 2000-128819 A | | 5/2000 |
| JP | 2000-128820 A | | 5/2000 |
| JP | 2003-221352 A | | 8/2003 |
| JP | 2008-21 4248 A | | 9/2008 |
| JP | 2008-285638 A | | 11/2008 |
| JP | 2010-248139 A | | 11/2010 |
| JP | 2010-261008 A | | 11/2010 |
| JP | 2012-214801 A | | 11/2012 |
| JP | 2014-114387 A | | 6/2014 |
| JP | 2015-051935 A | | 3/2015 |
| JP | 2018-090560 A | | 6/2018 |
| JP | 2018-145176 A | | 9/2018 |
| JP | 2018-145177 A | | 9/2018 |
| JP | 2018-145178 A | | 9/2018 |
| WO | WO-2014054311 A1 | * | 4/2014 ................ C08J 5/18 |

OTHER PUBLICATIONS

JP2010248139A (English translation), Nov. 4, 2010, pp. 1-6 (Year: 2010).*
WO2014/054311A1 (English translation), Apr. 10, 2014, pp. 1-21 (Year: 2014).*
JP2018145178A (English translation), Aug. 20, 2018 (Year: 2018).*
CN104591972A—English translation, May 6, 2015, pp. 1-6 (Year: 2015).*
International Search Report dated Oct. 30, 2018 in PCT/JP2018/031023 filed on Aug. 22, 2018, 3 pages.
Third Party Observation submitted Nov. 21, 2019 in PCT/JP2018/031023 filed on Aug. 22, 2018, 2 pages.
English translation of the International Preliminary Report on Patentability dated Mar. 5, 2020 in PCT/JP2018/031023 filed Aug. 22, 2018, 9 pages.

(Continued)

*Primary Examiner* — Medhanit W Bahta
(74) *Attorney, Agent, or Firm* — Oblon, McClelland, Maier & Neustadt, L.L.P.

(57) ABSTRACT

Provided is a thermally stable bisphenol composition whose increase in the Hazen color number is suppressed even under higher temperature conditions. A bisphenol composition including an aryl alkyl sulfide or a dialkyl disulfide at 0.1 ppb by mass to 1% by mass with respect to a bisphenol. A bisphenol composition including an aryl alkyl sulfide or a dialkyl disulfide at a predetermined ratio is thermally stable in terms of the Hazen color number, and shows no coloring problem under high temperature conditions. By using such a bisphenol composition, a polycarbonate resin having an excellent color tone can be produced.

12 Claims, No Drawings

(56) References Cited

OTHER PUBLICATIONS

Extended European Search Report dated Jul. 10, 2020 in European Patent Application No. 18849155.9, 8 pages.
Indian Office Action dated Aug. 4, 2021 in Indian Patent Application No. 202017011907 (with English translation), 8 pages.
Office Action and Search Report issued in the corresponding Chinese application No. 201680054304.2 dated Mar. 10, 2022 (with English machine translation).
Notice of Reasons for Refusal issued in corresponding Japanese Patent Application No. 2019-537659 dated Mar. 29, 2022, (with machine English translation).
Third-Party Observation submitted to the corresponding Japanese Patent Application No. 2019-537659 dated Sep. 2, 2022, (with its machine translation).
Third-Party Observation submitted to the corresponding Japanese Patent Application No. 2019-537659 dated Sep. 6, 2022, (with its machine translation).
Third-Party Observation submitted to the corresponding Japanese Patent Application No. 2019-537659 dated Sep. 13, 2022, (with its machine translation).
Notice of Reasons for Refusal dated Nov. 8, 2022, in the corresponding Japanese Patent Application No. 2019-537659, (with English machine translation).
Office Action was issued in the corresponding Chinese Patent Application No. 201880054304.2 dated Nov. 18, 2022 (with English machine translation).

* cited by examiner

BISPHENOL COMPOSITION AND METHOD FOR PRODUCING SAME, AND POLYCARBONATE RESIN AND METHOD FOR PRODUCING SAME

CROSS-REFERENCE TO RELATED APPLICATION

This is a continuation of International Application PCT/JP2018/031023, filed on Aug. 22, 2018, and designated the U.S., and claims priority from Japanese Patent Application 2017-159687 which was filed on Aug. 22, 2017 and Japanese Patent Application 2017-234313 which was filed on Dec. 6, 2017, the entire contents of which are incorporated herein by reference.

TECHNICAL FIELD

The present invention relates to a bisphenol composition containing a sulfide and a disulfide, and a method of producing it, and to a polycarbonate resin using the bisphenol composition, and a method of producing it.

The bisphenol composition as one embodiment of the present invention is useful as a resin raw material for polycarbonate resins, epoxy resins, aromatic polyester resins, and the like; and as an additive such as a curing agent, developer, discoloration inhibitor, microbicide, or antibacterial/antifungal agent.

BACKGROUND ART

Bisphenols are useful as raw materials of polymer materials such as polycarbonate resins, epoxy resins, and aromatic polyester resins. Known representative examples of bisphenols include 2,2-bis(4-hydroxyphenyl)propane and 2,2-bis(4-hydroxy-3-methylphenyl)propane (Patent Document 1). A method of producing 2,2-bis(4-hydroxy-3-methylphenyl)propane having a good hue (APHA) also is known (Patent Document 2).

PRIOR ART DOCUMENTS

Patent Documents

[Patent Document 1] JP 62-138443 A
[Patent Document 2] JP 2008-214248 A

SUMMARY OF THE INVENTION

Problems to be Solved by the Invention

The present inventors produced 2,2-bis(4-hydroxy-3-methylphenyl)propane by the method described in Patent Document 2. As a result, the Hazen color number was good, that is, there was no coloring problem, when melting was performed for 1 hour by heating at 150° C. It was found, however, that the Hazen color number increased (became poor) when the melting was performed for 2 hours by heating at 190° C., which is a reaction temperature during production of a common polycarbonate resin. Since a method of producing a polycarbonate resin by melting uses a raw material bisphenol in a molten state, thermal stability of the raw material bisphenol in terms of the Hazen color number is an important issue. Further, in uses as a resin raw material for epoxy resins, aromatic polyester resins, and the like, and also as an additive such as a curing agent, developer, or discoloration inhibitor, suppression of coloring is an important issue.

An object of the present invention is to provide a thermally stable bisphenol composition whose increase in the Hazen color number is suppressed even under higher temperature conditions.

Another object of the present invention is to provide a polycarbonate resin obtained by reacting a bisphenol composition, and a method of producing it.

Means for Solving the Problems

As a result of intensive study to solve the above problems, the present inventors discovered that, in cases where a bisphenol composition contains an alkyl aryl sulfide or a dialkyl disulfide at a predetermined ratio, the increase in the Hazen color number can be suppressed under conditions where the composition is heated at a temperature of as high as not less than 190° C. for not less than 2 hours in a molten state, thereby completing the present invention.

More specifically, the invention can be summarized as the following [1] to [10].

[1] A bisphenol composition comprising an aryl alkyl sulfide at 0.1 ppb by mass to 1% by mass with respect to a bisphenol.
[2] The bisphenol composition according to [1], wherein the aryl alkyl sulfide contains an aryl group which is a hydroxyphenyl group, a hydroxytolyl group, or a hydroxyxylyl group.
[3] The bisphenol composition according to [1] or [2], wherein the aryl alkyl sulfide contains a $C_8$-$C_{30}$ alkyl group.
[4] A bisphenol composition comprising a dialkyl disulfide at 0.1 ppb by mass to 1% by mass with respect to a bisphenol.
[5] The bisphenol composition according to [4], wherein the dialkyl disulfide contains a $C_8$-$C_{30}$ alkyl group.
[6] The bisphenol composition according to any one of [1] to [5], wherein the content of the bisphenol is not less than 95.0% by mass.
[7] A method of producing a bisphenol composition, comprising reacting a ketone or an aldehyde with an aromatic alcohol in the presence of an acid catalyst and an alkylthiol catalyst to produce the bisphenol composition according to any one of [1] to [6].
[8] The method of producing a bisphenol composition according to [7], wherein the acid catalyst is a monoalkyl sulfate.
[9] A method of producing a polycarbonate resin, comprising reacting the bisphenol composition according to any one of [1] to [6] to produce a polycarbonate resin.
[10] A polycarbonate resin comprising aryl alkyl sulfide structural units at not less than 1 ppb by mass with respect to bisphenol structural units.

Effect of the Invention

A bisphenol composition containing an aryl alkyl sulfide or a dialkyl disulfide at a predetermined ratio is thermally stable in terms of the Hazen color number, and shows no coloring problem under high temperature conditions. By using such a bisphenol composition, a polycarbonate resin having an excellent color tone can be produced.

MODE FOR CARRYING OUT THE INVENTION

Embodiments of the present invention are described below in detail, but the descriptions of the constituents described below are merely examples of modes of the present invention, and the present invention is not limited to the following descriptions as long as the spirit of the present invention is not spoiled.

In the present description, when the term "to" is used with values or physical property values before and after it, it is meant to include those values.

[Bisphenol Composition]

The bisphenol composition as one embodiment of the present invention (hereinafter also simply referred to as "bisphenol composition") contains an aryl alkyl sulfide or a dialkyl disulfide at 0.1 ppb by mass to 1% by mass with respect to a bisphenol.

The bisphenol composition, containing the predetermined amount of the aryl alkyl sulfide or the dialkyl disulfide, may also be a bisphenol composition containing the aryl alkyl sulfide and the dialkyl disulfide in a total amount of 0.1 ppb by mass to 1% by mass with respect to the bisphenol.

The aryl alkyl sulfide and/or the dialkyl disulfide may be hereinafter referred to as "(di)sulfide".

Since the bisphenol composition contains a bisphenol, and a (di)sulfide at 0.1 ppb by mass to 1% by mass with respect to the bisphenol, the composition may be referred to either as "bisphenol composition" or as "bisphenol containing a (di)sulfide".

<(Di)sulfide>

Examples of aryl alkyl sulfide include a 4-hydroxyphenyl alkyl sulfide which may contain a substituent, represented by the following General Formula (1).

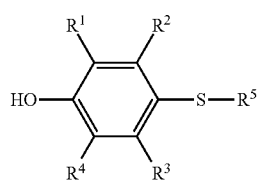

In General Formula (1), examples of $R^1$ to $R^4$ independently include a hydrogen atom, halogen atoms, alkyl groups, alkoxy groups, and aryl groups. Specific examples thereof include a hydrogen atom; halogen atoms such as fluoro, chloro, bromo, and iodo; $C_1$-$C_{20}$ linear or branched alkyl groups such as methyl, ethyl, n-propyl, i-propyl, n-butyl, i-butyl, t-butyl, n-pentyl, i-pentyl, n-hexyl, n-heptyl, n-octyl, n-nonyl, n-decyl, n-undecyl, and n-dodecyl; $C_3$-$C_{20}$ cyclic alkyl groups such as cyclopropyl, cyclobutyl, cyclopentyl, cyclohexyl, cycloheptyl, cyclooctyl, and cyclododecyl; $C_1$-$C_{20}$ linear or branched alkoxy groups such as methoxy, ethoxy, n-propoxy, i-propoxy, n-butoxy, i-butoxy, t-butoxy, n-pentyloxy, i-pentyloxy, n-hexyloxy, n-heptyloxy, n-octyloxy, n-nonyloxy, n-decyloxy, n-undecyloxy, and n-dodecyloxy; alkyl groups containing an aryl group as a substituent, such as benzyl; and aryl groups which may contain an alkyl group as a substituent, such as phenyl, tolyl, and 2,6-dimethylphenyl. Among these, $R^2$ and $R^3$ are preferably hydrogen atoms since, during production of the later-mentioned bisphenol product containing a (di)sulfide, the (di)sulfide production reaction hardly proceeds in cases where they are sterically bulky.

In General Formula (1), specific examples aryl groups which are 4-hydroxyphenyl having $R^1$ to $R^4$ include, but are not limited to, 4-hydroxyphenyl (wherein $R^1$ to $R^4$ are hydrogen atoms), 4-hydroxytolyl (wherein, for example, $R^1$ is methyl, and $R^2$ to $R^4$ are hydrogen atoms), and 4-hydroxyxylyl (wherein, for example, $R^1$ and $R^2$ are methyl, and $R^3$ and $R^4$ are hydrogen atoms)

In General Formula (1), $R^5$ is an alkyl group, and examples thereof include linear, branched, or cyclic alkyl groups which may contain an aryl group as a substituent, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, eicosyl, henicosyl, cyclodecyl, cyclododecyl, and benzyl. In cases where the alkyl group of $R^5$ has a small number of carbons, evaporation may occur by distillation during melting of the bisphenol composition. Thus, the alkyl group is an alkyl group having preferably not less than 8, especially preferably not less than 10 carbon atoms, such as octyl, nonyl, decyl, undecyl, or dodecyl. On the other hand, in cases where the alkyl group of $R^5$ has a large number of carbons, compatibility with the bisphenol decreases, so that $R^5$ is an alkyl group having preferably not more than 30, especially preferably not more than 20 carbon atoms. From the viewpoint of industrially producing $R^5$ at low cost, particularly it is preferably a chain alkyl group, more preferably a linear alkyl group.

Specific examples of the aryl alkyl sulfide include, but are not limited to, octyl(4-hydroxy-3-methylphenyl)sulfide, octyl(4-hydroxyphenyl)sulfide, nonyl(4-hydroxy-3-methylphenyl)sulfide, nonyl(4-hydroxyphenyl)sulfide, undecyl(4-hydroxy-3-methylphenyl)sulfide, decyl(4-hydroxyphenyl)sulfide, undecyl(4-hydroxy-3-methylphenyl)sulfide, decyl(4-hydroxyphenyl)sulfide, dodecyl(4-hydroxy-3-methylphenyl)sulfide, and dodecyl(4-hydroxyphenyl)sulfide; and those in which an alkyl group of these aryl alkyl sulfides is substituted with octyl, nonyl, decyl, undecyl, or dodecyl. Among the aryl alkyl sulfides, octyl(4-hydroxy-3-methylphenyl)sulfide, octyl(4-hydroxyphenyl)sulfide, nonyl(4-hydroxy-3-methylphenyl)sulfide, nonyl(4-hydroxyphenyl)sulfide, undecyl(4-hydroxy-3-methylphenyl)sulfide, decyl(4-hydroxyphenyl)sulfide, undecyl(4-hydroxy-3-methylphenyl)sulfide, decyl(4-hydroxyphenyl)sulfide, dodecyl(4-hydroxy-3-methylphenyl)sulfide, and dodecyl(4-hydroxyphenyl)sulfide; and those in which an alkyl group of these aryl alkyl sulfides is substituted with octyl, nonyl, decyl, undecyl, or dodecyl; are especially preferred since they can be included in a bisphenol product by allowing by-production in the reaction system in the later-mentioned production of a bisphenol.

The bisphenol composition may contain only one of the aryl alkyl sulfides, or may contain two or more of the aryl alkyl sulfides.

The dialkyl disulfide is represented by the following General Formula (2).

$$R^{5A}-S-S-R^{5B} \qquad (2)$$

In the General Formula (2), $R^{5A}$ and $R^{5B}$ may be either the same or different. These are preferably the same from the viewpoint of convenience during the synthesis and availability. Examples, and preferred examples, of $R^{5A}$ and $R^{5B}$ include those exemplified as $R^5$ in General Formula (1).

Specific examples of the dialkyl disulfide include, but are not limited to, didodecyl disulfide, didecyl disulfide, dinonyl disulfide, dioctyl disulfide, diundecyl disulfide. Among the dialkyl disulfides, didodecyl disulfide and didecyl disulfide are particularly preferred since they can be included in a bisphenol product by allowing by-production in the reaction system in the later-mentioned production of a bisphenol.

The bisphenol composition may contain only one of the dialkyl disulfides, or may contain two or more of the dialkyl disulfides. As described above, it may also be a composition containing one or more aryl alkyl sulfides and one or more dialkyl disulfides.

In the bisphenol composition, in cases where the content of the (di)sulfide with respect to the bisphenol is low, the thermal stability effect cannot be obtained in terms of the Hazen color number. Thus, the content is not less than 0.1 ppb by mass, preferably not less than 0.5 ppb by mass, more preferably not less than 1 ppb by mass, still more preferably not less than 10 ppb by mass. On the other hand, in cases where the content of the (di)sulfide with respect to the bisphenol is high, the molar ratio to diphenyl carbonate can be hardly controlled during production of a polycarbonate using the bisphenol composition containing the (di)sulfide. Thus, the content is not more than 1% by mass, preferably not more than 5000 ppm by mass, more preferably not more than 1000 ppm by mass.

More specifically, the Hazen color number is measured by the method described later in the Examples section.
<Bisphenol>

The bisphenol contained in the bisphenol composition is usually a compound represented by the following General Formula (3).

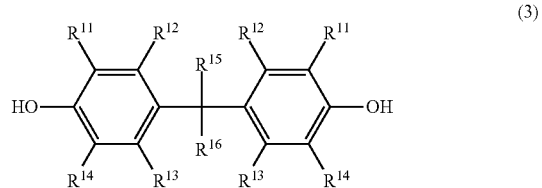

(3)

In the General Formula (3), $R^{11}$, $R^{12}$, $R^{13}$, and $R^{14}$ may be either the same or different. The two each of $R^{11}$, $R^{12}$, $R^{13}$, or $R^{14}$ present in General Formula (3) may be different from each other, but, from the viewpoint of convenience during the synthesis and availability, the two each of $R^{11}$, $R^{12}$, $R^{13}$, or $R^{14}$ are preferably the same. Examples, and preferred examples, of $R^{11}$ to $R^{14}$ include those exemplified as $R^1$ to $R^4$ in General Formula (1) (wherein $R^1$ corresponds to $R^{11}$; $R^2$ corresponds to $R^{12}$; $R^3$ corresponds to $R^{13}$; and $R^4$ corresponds to $R^{14}$). $R^{12}$ and $R^{13}$ are preferably protons since the condensation reaction hardly proceeds in cases where they are sterically bulky.

Examples of $R^{15}$ and $R^{16}$ independently include a hydrogen atom, alkyl groups, alkoxy groups, and aryl groups. Specific examples thereof include a hydrogen atom; $C_1$-$C_{20}$ linear or branched alkyl groups such as methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl, n-decyl, n-undecyl, and n-dodecyl; $C_3$-$C_{20}$ cyclic alkyl groups such as cyclopropyl, cyclobutyl, cyclopentyl, cyclohexyl, cycloheptyl, cyclooctyl, and cyclododecyl; $C_1$-$C_{20}$ linear or branched alkoxy groups such as methoxy, ethoxy, n-propoxy, i-propoxy, n-butoxy, i-butoxy, t-butoxy, n-pentyloxy, i-pentyloxy, n-hexyloxy, n-heptyloxy, n-octyloxy, n-nonyloxy, n-decyloxy, n-undecyloxy, and n-dodecyloxy; alkyl groups containing an aryl group as a substituent, such as benzyl; and aryl groups which may contain an alkyl group as a substituent, such as phenyl, tolyl, and 2,6-dimethylphenyl.

In General Formula (3), the two groups $R^{15}$ and $R^{16}$ may be bound or cross-linked to each other. Examples of such $R^{15}$ and $R^{16}$ include linking groups such as cyclopropylidene, cyclobutylidene, cyclopentylidene, cyclohexylidene, 3,3,5-trimethylcyclohexylidene, cycloheptylidene, cyclooctylidene, cyclononylidene, cyclodecylidene, cycloundecylidene, cyclododecylidene, fluorenylidene, xanthonilydene, and thioxanthonylidene.

Examples of the bisphenol contained in the bisphenol composition include, but are not limited to, 2,2-bis(4-hydroxyphenyl)propane, 2,2-bis(4-hydroxy-3-methylphenyl)propane, 1,1-bis(4-hydroxy-3-methylphenyl)cyclohexane, 9,9-bis(4-hydroxy-3-methylphenyl)fluorene, 3,3-bis(4-hydroxyphenyl)pentane, 3,3-bis(4-hydroxy-3-methylphenyl)pentane, 2,2-bis(4-hydroxyphenyl)pentane, 2,2-bis(4-hydroxy-3-methylphenyl)pentane, 3,3-bis(4-hydroxyphenyl)heptane, 3,3-bis(4-hydroxy-3-methylphenyl)heptane, 2,2-bis(4-hydroxyphenyl)heptane, 2,2-bis(4-hydroxy-3-methylphenyl)heptane, 4,4-bis(4-hydroxyphenyl)heptane, and 4,4-bis(4-hydroxy-3-methylphenyl)heptane.

The bisphenol composition contains a bisphenol as a major component, and the bisphenol is usually contained at not less than 95.0% by mass in the bisphenol composition. The content of the bisphenol in the bisphenol composition is preferably not less than 97.0% by mass, more preferably not less than 98.0% by mass, still more preferably not less than 98.5% by mass, most preferably not less than 99.0% by mass.

The content of components other than the bisphenol and the aromatic alcohol sulfonate in the bisphenol composition is preferably low.

In particular, for use as a raw material of a polycarbonate resin, the content of components that inhibit polymerization with diester carbonate is preferably low in the bisphenol composition.
<Method of Producing Bisphenol Composition>

The method of producing a bisphenol composition is not limited, and examples of the method include the following.

(1) A method in which a predetermined amount of a (di)sulfide is added to a solid bisphenol.

(2) A method in which a predetermined amount of a (di)sulfide is added to a molten bisphenol.

(3) A method in which a (di)sulfide is by-produced during production of a bisphenol, to obtain a bisphenol product containing the (di)sulfide.

In the methods (1) and (2), wherein a (di)sulfide is added to a solid or molten bisphenol, the (di)sulfide needs to be separately provided. Therefore, the method (3), wherein a (di)sulfide is by-produced in a reaction system for production of a bisphenol, to thereby include the (di)sulfide in a bisphenol product, is preferred.

In cases where the (di)sulfide by-produced in the bisphenol reaction system is too much, the resulting bisphenol product may be further subjected to crystallization, suspension washing, and sprinkle-washing to remove part of the (di)sulfide contained in the bisphenol product, thereby controlling the composition such that a bisphenol product containing the (di)sulfide within the range specified in the present invention can be obtained.
<Method of Obtaining Bisphenol Product Containing (Di) Sulfide>

Examples of the method in which a (di)sulfide is produced together with a bisphenol in the reaction system during production of the bisphenol, to obtain a bisphenol product containing the (di)sulfide as a bisphenol composition, include a method in which a ketone or an aldehyde is condensed with an aromatic alcohol in the presence of an acid catalyst and a thiol catalyst, to produce a bisphenol. By this method, a (di)sulfide derived from the thiol catalyst can be produced in the reaction system.

This method is described below.

In this method, an aromatic alcohol is condensed with a ketone or an aldehyde preferably using sulfuric acid as a catalyst, and a thiol as a promoter, and more preferably, further using an aliphatic alcohol, to produce a bisphenol.

The production reaction of a bisphenol is carried out according to the following Reaction Formula (4). In this reaction, by using, for example, an alkanethiol represented by RSH (wherein R preferably represents a $C_8$-$C_{30}$ alkyl) as a thiol, an aryl alkyl sulfide represented by the following General Formula (1A) can be produced as a (di)sulfide.

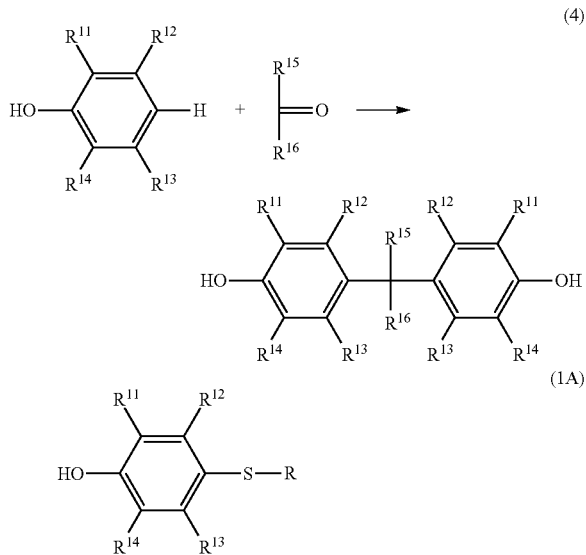

(4)

(1A)

(In the formulae, $R^{11}$ to $R^{16}$ have the same meanings as in General Formula (3).)

The aromatic alcohol used as a raw material of the bisphenol is usually a compound represented by the following General Formula (5).

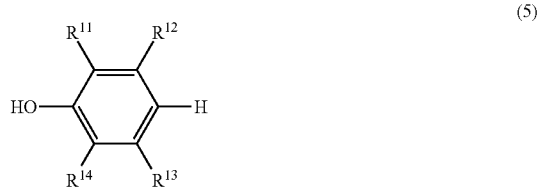

(5)

(In the formula, $R^{11}$ to $R^{14}$ have the same meanings as in General Formula (3).)

The ketone or the aldehyde is usually a compound represented by the following General Formula (6).

(6)

(In the formula, $R^{15}$ and $R^{16}$ have the same meanings as in General Formula (3).)

In the reaction of condensing the aromatic alcohol with the ketone or the aldehyde, in cases where the molar ratio of the aromatic alcohol to the ketone or the aldehyde is low, the ketone or the aldehyde undergoes multimerization, while in cases where the ratio is high, unreacted aromatic alcohol is lost. From these reasons, the molar ratio of the aromatic alcohol to the ketone or the aldehyde is preferably not less than 1.5, more preferably not less than 1.6, still more preferably a molar ratio of not less than 1.7, and is preferably not more than 15, more preferably not more than 10, still more preferably not more than 8.

This method of feeding the ketone or the aldehyde may be a method in which the ketone or the aldehyde is fed at once, or may be a method in which the ketone or the aldehyde is fed dividedly. Since the reaction for producing the bisphenol is an exothermic reaction, the method is preferably a method in which the ketone or the aldehyde is fed dividedly by, for example, slowly feeding it in a dropwise manner.

The sulfuric acid used as the catalyst may be a concentrated sulfuric acid. However, in cases where the concentration of the sulfuric acid is too high, multimerization of the ketone or the aldehyde and dehydration dimerization of the aliphatic alcohol are promoted, causing deterioration of the thiol and sulfonation of the produced bisphenol. On the other hand, in cases where the concentration of the sulfuric acid used is too low, the reaction time increases, and therefore the bisphenol cannot be produced efficiently. Thus, the concentration of the sulfuric acid used is preferably not less than 50% by mass, more preferably not less than 60% by mass, and is preferably not more than 95% by mass, more preferably not more than 90% by mass.

In cases where the molar ratio of the sulfuric acid to the ketone or the aldehyde is low, dilution of the sulfuric acid occurs with water by-produced during the condensation reaction, leading to requirement of a long reaction time. In cases where the molar ratio is high, multimerization of the ketone or the aldehyde proceeds. From these reasons, the molar ratio of the sulfuric acid to the ketone or the aldehyde is preferably not less than 0.0001, more preferably not less than 0.01, still more preferably not less than 0.05, especially preferably not less than 0.1, and is preferably not more than 10, more preferably not more than 8, still more preferably not more than 5, especially preferably not more than 3.

In this reaction, it is preferred to use an aliphatic alcohol, and to use a monoalkyl sulfate, as a catalyst, produced by reaction between the sulfuric acid and the aliphatic alcohol from the viewpoint of controlling the acid strength of the catalyst and suppressing condensation (multimerization) and coloring of the raw material ketone or aldehyde, to enable simple and efficient production of a bisphenol while reducing production of side reaction products and coloring of the resulting product. In the present application, the method in which the bisphenol is prepared utilizing the reaction between the sulfuric acid and the aliphatic alcohol is also referred to as "sulfuric acid alcohol method". For example, in a case where reaction between sulfuric acid and methanol is utilized, the method is also referred to as sulfuric acid methanol method (sulfuric acid MET method). Further, with the residual content of the aliphatic alcohol used for the generation of the monoalkyl sulfate, the produced bisphenol can be dissolved to suppress solidification of the reaction liquid, and the mixed state can be improved, thereby enabling shortening of the reaction time, which is advantageous.

Examples of the monoalkyl sulfate include monomethyl sulfate, monoethyl sulfate, monopropyl sulfate, monoisopropyl sulfate, monobutyl sulfate, monoisobutyl sulfate, mono t-butyl sulfate, monopentyl sulfate, monoisopentyl sulfate, monohexyl sulfate, monoheptyl sulfate, monooctyl sulfate, monononyl sulfate, monodecyl sulfate, monoundecyl sulfate, monododecyl sulfate, mono(hydroxyethyl) sulfate, mono(2-hydroxyethoxyethyl) sulfate, and mono(2-(2'-hydroxyethoxy)ethoxyethyl) sulfate. Among these, monoalkyl sulfates having not more than 8 carbon atoms are preferably used since, in cases where the number of carbons is large, lipophilicity increases, and therefore transfer of the monoalkyl sulfate between the organic phase and the aqueous phase becomes difficult.

The method of producing the monoalkyl sulfate is not limited, and, from the viewpoint of obtaining the monoalkyl sulfate at low cost, one example of the method is a method in which the monoalkyl sulfate is produced by reaction between sulfuric acid and an aliphatic alcohol.

The concentration of the monoalkyl sulfate in the reaction liquid is preferably 0.0001% by weight to 50% by weight.

Examples of the aliphatic alcohol include $C_1$-$C_{12}$ alkyl alcohols such as methanol, ethanol, n-propanol, i-propanol, n-butanol, i-butanol, t-butanol, n-pentanol, i-pentanol, n-hexanol, n-heptanol, n-octanol, n-nonanol, n-decanol, n-undecanol, n-dodecanol, ethylene glycol, diethylene glycol, and triethylene glycol. As the number of carbon atoms in the aliphatic alcohol increases, lipophilicity increases. In such a case, the aliphatic alcohol can be hardly mixed with sulfuric acid, and therefore the monoalkyl sulfate can be hardly obtained. Thus, the aliphatic alcohol is preferably an alkyl alcohol having not more than 8 carbon atoms.

As described above, the aliphatic alcohol is used as a monoalkyl sulfate by mixing and reacting with sulfuric acid. In cases where the molar ratio of the aliphatic alcohol to the sulfuric acid is low, the amount of the monoalkyl sulfate produced is small, so that the reaction takes a long time, while in cases where the molar ratio is high, the sulfuric acid concentration is low. From these reasons, the molar ratio of the aliphatic alcohol to the sulfuric acid is preferably not less than 0.01, more preferably not less than 0.05, still more preferably not less than 0.1, and is preferably not more than 10, more preferably not more than 5, still more preferably not more than 3.

The concentration of the aliphatic alcohol in the reaction liquid is preferably not less than 0.01% by weight, more preferably not less than 0.05% by weight, and is preferably not more than 40% by weight, more preferably not more than 20% by weight.

Examples of the thiol used as a promoter include mercaptocarboxylic acids such as mercaptoacetic acid, thioglycolic acid, 2-mercaptopropionic acid, 3-mercaptopropionic acid, and 4-mercaptobutyric acid; methyl mercaptan, ethyl mercaptan, propyl mercaptan, butyl mercaptan, pentyl mercaptan, hexyl mercaptan, heptyl mercaptan, octyl mercaptan, nonyl mercaptan, decyl mercaptan (decanethiol), undecyl mercaptan (undecanethiol), dodecyl mercaptan (dodecanethiol), tridecyl mercaptan, tetradecyl mercaptan, and pentadecyl mercaptan. For allowing by-production of a (di)sulfide suitable for the above embodiment, an alkanethiol containing a $C_8$-$C_{30}$, especially $C_{10}$-$C_{20}$ alkyl group is preferably used.

The concentration of the thiol in the reaction liquid is preferably not less than 0.01% by weight, more preferably not less than 0.1% by weight, and is preferably not more than 20% by weight, more preferably not more than 10% by weight.

In cases where the molar ratio of the thiol to the ketone or the aldehyde is low, the selectivity-improving effect by the use of the thiol promoter cannot be obtained, while in cases where the molar ratio is high, the quality is deteriorated due to contamination in the bisphenol. From these reasons, the molar ratio of the thiol to the ketone and the aldehyde is preferably not less than 0.001, more preferably not less than 0.005, still more preferably not less than 0.01, and is preferably not more than 1, more preferably not more than 0.5, still more preferably not more than 0.1.

From the viewpoint of suppressing oxidative degradation of the thiol, the thiol is preferably preliminarily mixed with the ketone or the aldehyde before being subjected to the reaction. Regarding the method for feeding the thiol and the ketone or the aldehyde, the ketone or the aldehyde may be mixed into the thiol, or the thiol may be mixed into the ketone or the aldehyde. Regarding the method for mixing the mixed liquid of the thiol and the ketone or the aldehyde with the sulfuric acid, the sulfuric acid may be mixed into the mixed liquid, or the mixed liquid may be mixed into the sulfuric acid. Preferably, the mixed liquid is mixed into the sulfuric acid. More preferably, after the sulfuric acid and the aromatic alcohol are fed to the reaction vessel, the mixed liquid is fed to the reaction vessel to be mixed.

The bisphenol production reaction may be carried out in the presence of a solvent such as toluene or xylene. The solvent that has been used for the production of the bisphenol may be recovered by distillation or the like, and then purified for reusing it.

Alternatively, without using the solvent, a large amount of the raw material aromatic alcohol may be used instead of the solvent. In such cases, loss of unreacted aromatic alcohol occurs. For reducing the loss, it may be recovered by distillation or the like, and then purified for reusing it.

The bisphenol production reaction is a condensation reaction. In cases where the reaction temperature during the production reaction is too high, oxidative degradation of the thiol proceeds, while in cases where the reaction temperature is too low, the reaction takes a long time. Thus, the reaction temperature is preferably 0° C. to 50° C.

In cases where the reaction time of the production reaction is too long, degradation of the produced bisphenol occurs. Thus, the reaction time is preferably not more than 30 hours, more preferably not more than 25 hours, still more preferably not more than 20 hours. Regarding the lower limit of the reaction time, the reaction time is usually not less than 15 hours. By adding water in an amount equivalent to or larger than the amount of the sulfuric acid used, the sulfuric acid concentration can be reduced to stop the reaction.

Purification of the bisphenol product obtained by the bisphenol production reaction may be carried out by an ordinary method. For example, the bisphenol may be purified by simple means such as crystallization or column chromatography. More specifically, after the condensation reaction, an organic phase obtained by separation of the reaction liquid is washed with water, brine, or the like, and then, if necessary, neutralized by washing with aqueous sodium bicarbonate or the like. Subsequently, the washed organic phase is cooled to allow crystallization. In cases where a large amount of aromatic alcohol is used, excessive aromatic alcohol is evaporated by distillation before the crystallization.

For allowing the (di)sulfide by-produced in the bisphenol production reaction system to remain to thereby obtain the bisphenol product containing the (di)sulfide as a bisphenol composition, the purification conditions in the above purification method for the bisphenol product are preferably controlled such that a predetermined amount of the (di) sulfide remains in the purified bisphenol product by performing, for example, crystallization, suspension washing, and sprinkle-washing.

<Use of Bisphenol Composition>

The bisphenol composition can be used as a component of, for example, a variety of thermoplastic resins such as polyether resins, polyester resins, polyarylate resins, polycarbonate resins, polyurethane resins, and acrylic resins, and a variety of thermosetting resins such as epoxy resins, unsaturated polyester resins, phenol resins, polybenzoxazine resins, and cyanate resins; as a curing agent; as an additive; or as a precursor thereof; to be used for various uses including optical materials, recording materials, insulating materials, transparent materials, electronic materials, adhesive materials, and heat-resisting materials. The bisphenol composition is also useful as a developer or a discoloration inhibitor for thermal recording materials and the like; or as an additive such as a microbicide or an antibacterial/antifungal agent.

Among these, from the viewpoint of giving favorable mechanical properties, use as a raw material (monomers) of a thermoplastic resin or a thermosetting resin is preferred. In particular, use as a raw material of a polycarbonate resin or an epoxy resin is more preferred. Use as a developer is also preferred. In particular, use in combination with a leuco dye or a color change temperature regulator is more preferred.

[Polycarbonate Resin and Production Method Therefor]

A polycarbonate resin using a bisphenol composition as a raw material, and a production method therefor are described below.

The polycarbonate resin as one embodiment of the present invention is a polycarbonate resin comprising aryl alkyl sulfide structural units at not less than 1 ppb by mass with respect to bisphenol structural units.

The polycarbonate resin using a bisphenol composition as a raw material can be produced by reacting the above-mentioned bisphenol composition. The production can be manufactured by, for example, a method in which the bisphenol composition and a diester carbonate such as diphenyl carbonate are subjected to transesterification reaction in the presence of an alkali metal compound and/or an alkaline earth metal compound. The transesterification reaction may be carried out by appropriately selecting a known method. One example using the bisphenol composition and diphenyl carbonate as raw materials is described below.

From the viewpoint of securing an excellent color tone, the content of dialkyl disulfide structural units or aryl alkyl sulfide structural units with respect to bisphenol structural units in the resin is preferably not less than 1 ppb by mass, more preferably not less than 5 ppb by mass, still more preferably not less than 8 ppb by mass, still more preferably not less than 10 ppb by mass, especially preferably not less than 20 ppb by mass, and is not more than 1.0% by mass, preferably not more than 100 ppm by mass, more preferably not more than 80 ppm by mass, still more preferably not more than 50 ppm by mass.

In the method of producing a polycarbonate resin, diphenyl carbonate is preferably used in an excess amount with respect to the bisphenol in the bisphenol composition. The amount of the diphenyl carbonate used with respect to the bisphenol is preferably large from the viewpoint of producing a polycarbonate resin having less terminal hydroxyl groups and achieving excellent thermal stability of the polymer, but preferably small from the viewpoint of increasing the transesterification reaction rate and easily producing a polycarbonate resin having a desired molecular weight. From these reasons, the amount of the diphenyl carbonate used with respect to 1 mol of the bisphenol is usually not less than 1.001 mol, preferably not less than 1.002 mol, and is usually not more than 1.3 mol, preferably not more than 1.2 mol.

Regarding the method of feeding the raw materials, the bisphenol composition and the diphenyl carbonate may be fed as solids, but it is preferred to melt one or both, and to feed it/them in a liquid state. As described above, the bisphenol composition is thermally stable, and shows a small increase in the Hazen color number even by heat melting during which the composition is exposed to high-temperature conditions for a long time, so that there is no coloring problem. Thus, the composition is especially effective when it is fed in a molten state.

When a polycarbonate resin is produced by transesterification reaction between the diphenyl carbonate and the bisphenol, a catalyst is usually used. In the method of producing a polycarbonate resin, an alkali metal compound(s) and/or an alkaline earth metal compound(s) is/are preferably used as the transesterification catalyst. These may be used either individually, or as an arbitrary combination of two or more at an arbitrary ratio. Practically, an alkali metal compound(s) is/are preferably used.

The amount of the catalyst used with respect to 1 mol of the bisphenol or the diphenyl carbonate is usually not less than 0.05 μmol, preferably not less than 0.08 μmol, more preferably not less than 0.10 μmol, and is usually not more than 100 μmol, preferably not more than 50 μmol, more preferably not more than 20 μmol.

In cases where the amount of the catalyst used is within the range described above, polymerization activity required for production of a polycarbonate resin having a desired molecular weight can be easily obtained, and a polycarbonate resin can be easily obtained with an excellent polymer hue, without excessive branching of the polymer, and with excellent fluidity during molding.

For production of a polycarbonate resin by the above method, it is preferred to feed both raw materials continuously to a raw-material mixing vessel, and then to feed the resulting mixture and the transesterification catalyst continuously to a polymerization vessel.

Usually, in the production of the polycarbonate resin by the transesterification method, both raw materials fed to the raw-material mixing vessel are uniformly stirred, and then fed to the polymerization vessel where the catalyst is added, to produce a polymer.

Since the bisphenol composition contains the (di)sulfide, it shows a suppressed increase in the Hazen color number (shows less coloring) upon melting. Therefore, a less-colored polycarbonate resin can be obtained by polycondensing the bisphenol composition with diphenyl carbonate in the presence of the transesterification catalyst.

EXAMPLES

The present invention is described below more concretely by way of Examples and Comparative Examples. However, the present invention is not limited by the following Examples as long as the spirit of the present invention is not spoiled.

[Raw Materials and Reagents]

In the following Examples and Comparative Examples, as dodecanethiol, ethanol, iodine, methylene chloride, sodium thiosulfate, sodium chloride, magnesium sulfate, acetone, acetonitrile, ortho-cresol, sodium thiocyanate, methanol, bromine, sodium bromide, ethyl acetate, lithium hydride, tetrahydrofuran, hydrochloric acid, sodium bicarbonate (sodium hydrogen carbonate), cesium carbonate, hexane, ortho-xylene, 2,2-bis(4-hydroxy-3-methylphenyl)propane (hereinafter referred to as bisphenol C), ortho-xylene, sulfuric acid, toluene, and cyclohexanone, reagents manufactured by Wako Pure Chemical Industries, Ltd. were used.

As 1-bromododecane, 4-hydroxythiophenol, 1-bromodecane, decyl disulfide, 9-fluorenone, 1,1-bis(4-hydroxy-3-methylphenyl)cyclohexane, and 9,9-bis(4-hydroxy-3-methylphenyl)fluorene, reagents manufactured by Tokyo Chemical Industry Co., Ltd. were used.

As diphenyl carbonate, a product manufactured by Mitsubishi Chemical Corporation was used.

[Analysis]

<Composition Analysis of Bisphenol Product>

Composition analysis of the bisphenol product (reaction product liquid) was carried out by high-performance liquid chromatography by the following procedure under the following conditions.

Apparatus: LC-2010A, Imtakt Scherzo SM-C18 3 μm 150 mm×4.6 mm ID, manufactured by Shimadzu Corporation
  Low-pressure gradient method
  Analysis temperature: 40° C.
  Eluent composition
  Liquid A, solution of ammonium acetate:acetic acid: demineralized water=3.000 g:1 mL:1 L
  Liquid B, solution of ammonium acetate:acetic acid: acetonitrile=1.500 g:1 mL:900 mL
  At Minute 0 of the analysis time, Liquid A:Liquid B=60: 40 (volume ratio, the same applies hereinafter).
  From Minute 0 to Minute 25 during the analysis time, the eluent composition was gradually changed to Liquid A:Liquid B=90:10.
  From Minute 25 to Minute 30 during the analysis time, the composition was maintained at Liquid A:Liquid B=90:10.
  The analysis was carried out at a flow rate of 0.8 mL/min.

<Reaction Yield (Mol %) of Bisphenol in Terms of Acetone>

The reaction yield (mol %) of bisphenol C in terms of acetone was determined by calculating the bisphenol C concentration in the reaction liquid based on the peak detected at a wavelength of 280 nm by high-performance liquid chromatography, calculating, from the concentration, the molar amount of the bisphenol C contained in the bisphenol C production reaction liquid, and then performing the following calculation: the molar amount of the bisphenol C÷the molar amount of the raw material acetone×100%.

The amount of 1,1-bis(4-hydroxy-3-methylphenyl)cyclohexane or 9,9-bis(4-hydroxy-3-methylphenyl)fluorene produced was determined by calculating % by area from the area of the peak detected at a wavelength of 280 nm in high-performance liquid chromatography.

Identification of Dodecyl(4-Hydroxy-3-Methylphenyl)Sulfide, Decyl(4-Hydroxyphenyl)Sulfide, and Decyl(4-Hydroxyphenyl)Sulfide Identification of dodecyl(4-hydroxy-3-methylphenyl)sulfide, decyl(4-hydroxyphenyl)sulfide, and decyl(4-hydroxyphenyl)sulfide was carried out using a gas chromatograph-mass spectrometer by the following procedure under the following conditions.

As an apparatus, "Agilent 6890", manufactured by Agilent Technologies, Inc. was used. As a column, "DB-1MS", manufactured by Agilent Technologies, Inc. (0.25-mm inner diameter×30 m×0.25 μm) was used. As a carrier gas, helium was used. Its flow rate was set to 1 cm$^3$ per minute. The inlet temperature was set to 280° C.; the transfer temperature was set to 250° C.; and the ion source temperature was set to 250° C. The column heating pattern was as follows. First, the temperature was kept at 60° C. for 3 minutes. Thereafter, the temperature was increased to 280° C. at 10° C. per minute, and then kept at 280° C. for 5 minutes to perform the analysis.

Analysis of Dodecyl(4-Hydroxy-3-Methylphenyl)Sulfide

Analysis of dodecyl(4-hydroxy-3-methylphenyl)sulfide was carried out by gas chromatography by the following procedure under the following conditions.

As an apparatus, "GC-17A", manufactured by Shimadzu Corporation was used. As a column, "DB-1", manufactured by Agilent Technologies, Inc. (inner diameter, 0.53 mm; column length, 30 m; film thickness, 1 μm) was used. As a carrier gas, helium was used. Its flow rate was set to 5.58 cm$^3$ per minute, and its linear velocity was set to 47.4 cm per second. The inlet temperature was set to 250° C., and the detector temperature was set to 280° C. The column heating pattern was as follows. First, the temperature was kept at 150° C. for 5 minutes. Thereafter, the temperature was increased to 295° C. at 13° C. per minute, and then kept at 295° C. for 15 minutes to perform the analysis.

<Measurement of Hazen Color Number Upon Melting of Bisphenol Composition or Bisphenol>

Measurement of the Hazen color number upon melting of the bisphenol composition or the bisphenol was carried out using a color difference meter by the following procedure under the following conditions.

As a test tube for a spectroscopic color difference meter, a test tube manufactured by Nichiden Rika Glass (24 mm×200 m/m P-24) was used. As an apparatus, "SE-6000", manufactured by Nippon Denshoku Industries Co., Ltd. was used. Regarding the measurement of the Hazen color number, a bisphenol or a bisphenol composition (bisphenol product) was placed in the test tube for a spectroscopic color difference meter, and the test tube was heated at a predetermined temperature on an aluminum block heater, followed by performing the measurement within 30 seconds after a predetermined length of time.

Regarding the concentration of the aryl alkyl sulfide or the dialkyl disulfide contained in the bisphenol C, in cases where no particular treatment is carried out for the subject to be measured, the detection limit is usually 0.1 ppm. However, by performing treatment such as concentration, the detection limit can be 0.5 ppb.

Reference Example 1

Didodecyl disulfide (hereinafter referred to as C12SSC12) was synthesized with reference to Langmuir 2001, 17, 7735-7741.

In a 500-mL recovery flask equipped with a magnetic stirring bar, 20 g (0.1 mol) of dodecanethiol and 200 mL of ethanol were placed to obtain a solution. Iodine was slowly added thereto at room temperature until the solution was colored. Thereafter, the resulting mixture was stirred for 30 minutes. Methylene chloride was added to the solution, and the resulting mixture was washed three times with saturated aqueous sodium thiosulfate solution, and then twice with saturated brine. The obtained organic phase was dried over magnesium sulfate. Part of the obtained organic phase was taken and subjected to measurement by gas chromatography. As a result, a peak was detected at the same retention time as the reagent C12SSC12 manufactured by Angene International Limited, indicating production of C12SSC12. A low-boiling fraction was evaporated from the organic phase using an evaporator, and the resulting residue was subjected to three times of recrystallization using acetone and acetonitrile, followed by drying to obtain 15 g of C12SSC12.

Reference Example 2

Dodecyl(4-hydroxy-3-methylphenyl)sulfide (hereinafter referred to as C12SoCRS) was synthesized as follows.

In a 500-mL recovery flask equipped with a magnetic stirring bar and a dropping funnel, 34 g (0.3 mol) of ortho-cresol, 82 g (1.0 mol) of sodium thiocyanate, and 174 g of methanol were placed. In the dropping funnel, 50 g (0.3 mol) of bromine, 300 g of methanol, and 32 g of sodium bromide were placed. The recovery flask was placed in an ice bath, and the bromine solution was slowly fed dropwise from the dropping funnel. Thereafter, the resulting mixture was mixed by stirring for 6 hours. Demineralized water was added to the resulting reaction mixture, and then extraction was carried out with ethyl acetate. The obtained organic phase was dried over magnesium sulfate, and then concentrated under reduced pressure. In a 500-mL recovery flask equipped with a magnetic stirring bar and a dropping funnel, 7.5 g (0.2 mol) of lithium hydride and 100 g of tetrahydrofuran were placed, and the obtained concentrate and 100 g of tetrahydrofuran were placed in the dropping funnel. The flask was placed in an ice bath, and the solution of the concentrate in the tetrahydrofuran was slowly fed dropwise thereto. Thereafter, the resulting mixture was stirred for 1 hour, and dilute hydrochloric acid was slowly added thereto, followed by further extraction with ethyl acetate. The obtained organic phase was neutralized with saturated sodium bicarbonate solution, and then washed with water, followed by drying over magnesium sulfate and concentration under reduced pressure. The resulting residue was purified by distillation by Kugelrohr distillation, to obtain 13.6 g of 4-hydroxy-3-methylphenylmercaptan as an intermediate.

To a 500-mL recovery flask equipped with a magnetic stirring bar, 13.6 g (0.1 mol) of the intermediate, 28 g (0.1 mol) of cesium carbonate, 18 g (0.1 mol) of 1-bromododecane, and 160 mL of acetonitrile were placed. The resulting slurry solution was stirred at room temperature for 18 hours, and then 10% by mass hydrochloric acid was added thereto to stop the reaction. To the resulting mixture, ethyl acetate was added to perform extraction. The obtained organic phase was washed with saturated sodium bicarbonate solution, water, and then saturated brine, followed by dehydration with magnesium sulfate. Part of the obtained organic phase was taken and subjected to measurement using a gas chromatograph-mass spectrometer. As a result, a mass number of 280 ($M^+$) was found by the electron impact method, indicating production of C12SoCRS. From the remaining part of the dehydrated organic phase, a low-boiling fraction was evaporated using an evaporator. As a result, a white solid was obtained. The white solid was subjected to three times of recrystallization using hexane, followed by drying to obtain 5 g of C12SoCRS.

Reference Example 3

Decyl(4-hydroxyphenyl)sulfide (hereinafter referred to as C10SPhl) was synthesized with reference to Example 13 of WO 2000/034254.

To a 500-mL recovery flask equipped with a magnetic stirring bar, 11 g (87 mmol) of 4-hydroxythiophenol, 19 g (86 mmol) of 1-bromodecane, 28 g of cesium carbonate, and 160 mL of acetonitrile were placed, to obtain a slurry solution. The slurry solution was stirred at room temperature for 18 hours, and then 10% by mass hydrochloric acid was added thereto to stop the reaction. To the resulting mixture, ethyl acetate was added to perform extraction. The obtained organic phase was washed with saturated sodium bicarbonate solution, water, and then saturated brine, followed by dehydration with magnesium sulfate. Part of the dehydrated organic phase was taken and subjected to measurement using a gas chromatograph-mass spectrometer. As a result, a mass number of 266 ($M^+$) was found by the electron impact method, indicating production of C10SPhl. From the remaining part of the dehydrated organic phase, a low-boiling fraction was evaporated using an evaporator. As a result, a white solid was obtained. The white solid was subjected to three times of recrystallization using hexane, followed by drying to obtain 10 g of C10SPhl.

Reference Example 4

Dodecyl(4-hydroxyphenyl)sulfide (hereinafter referred to as C12SPhl) was synthesized with reference to Example 13 of WO 2000/034254.

To a 500-mL recovery flask equipped with a magnetic stirring bar, 13 g (104 mmol) of 4-hydroxythiophenol, 33 g (117 mmol) of 1-bromododecane, 40 g of cesium carbonate, and 200 mL of acetonitrile were placed, to obtain a slurry solution. The slurry solution was stirred at room temperature for 18 hours, and then 10% by mass hydrochloric acid was added thereto to stop the reaction. To the resulting mixture, ethyl acetate was added to perform extraction. The obtained organic phase was washed with saturated sodium bicarbonate solution, water, and then saturated brine, followed by dehydration with magnesium sulfate. Part of the dehydrated organic phase was taken and subjected to measurement using a gas chromatograph-mass spectrometer. As a result, a mass number of 294 ($M^+$) was found by the electron impact method, indicating production of C12SPhl. From the remaining part of the dehydrated organic phase, a low-boiling fraction was evaporated using an evaporator. As a result, a white solid was obtained. The white solid was subjected to three times of recrystallization using hexane, followed by drying to obtain 15 g of C12SPhl.

Example 1

In a test tube for a spectroscopic color difference meter, 15 g of bisphenol C as a reagent and 1.3 mg of the dodecyl(4-hydroxy-3-methylphenyl)sulfide (C12SoCRS) synthesized in Reference Example 2 were placed, and the test tube was then placed on an aluminum block heater set to 194° C., to prepare a molten liquid of bisphenol C. Fifteen minutes after the beginning of the heating, the molten liquid was subjected to measurement using the color difference meter. As a result, the Hazen color number (APHA) was found to be 40. The solution was further heated for 2 hours, and then the molten liquid was subjected to measurement using the color difference meter. As a result, the Hazen color number (APHA) was found to be 50.

Example 2

In a test tube for a spectroscopic color difference meter, 15 g of bisphenol C as a reagent and 1.7 mg of the decyl(4-hydroxyphenyl)sulfide (C12SPhl) synthesized in Reference Example 3 were placed, and the test tube was then placed on an aluminum block heater set to 194° C., to prepare a molten liquid of bisphenol C. Fifteen minutes after the beginning of the heating, the molten liquid was subjected to measurement using the color difference meter. As a result, the Hazen color number (APHA) was found to be 50. The solution was further heated for 2 hours, and then the molten liquid was subjected to measurement using the color difference meter. As a result, the Hazen color number (APHA) was found to be 70.

Example 3

In a test tube for a spectroscopic color difference meter, 15 g of bisphenol C as a reagent and 5.3 mg of the dodecyl(4-hydroxyphenyl)sulfide (C10SPhl) synthesized in Reference Example 4 were placed, and the test tube was then placed on an aluminum block heater set to 194° C., to prepare a molten liquid of bisphenol C. Fifteen minutes after the beginning of the heating, the molten liquid was subjected to measurement using the color difference meter. As a result, the Hazen color number (APHA) was found to be 50. The solution was further heated for 2 hours, and then the molten liquid was subjected to measurement using the color difference meter. As a result, the Hazen color number (APHA) was found to be 75.

Example 4

In a test tube for a spectroscopic color difference meter, 7.5 g of 1,1-bis(4-hydroxyphenyl)cyclohexane as a reagent, 7.5 g of diphenyl carbonate, and 10 mg of dodecyl(4-hydroxyphenyl)sulfide (C12SPhl) were placed, and the test tube was then placed on an aluminum block heater set to 194° C., to prepare a molten liquid. Fifteen minutes after the beginning of the heating, the molten liquid was subjected to measurement using the color difference meter. As a result, the Hazen color number (APHA) was found to be 15. The molten liquid was further heated for 2 hours, and then subjected to measurement using the color difference meter. As a result, the Hazen color number (APHA) was found to be 25.

Comparative Example 1

In a test tube for a spectroscopic color difference meter, 15 g of bisphenol C as a reagent (manufactured by Wako Pure Chemical Industries, Ltd.) was placed, and the test tube was then placed on an aluminum block heater set to 194° C., to prepare a molten liquid of bisphenol C. Fifteen minutes after the beginning of the heating, the molten liquid was subjected to measurement using the color difference meter. As a result, the Hazen color number (APHA) was found to be 60. The solution was further heated for 2 hours, and then the molten liquid was subjected to measurement using the color difference meter. As a result, the Hazen color number (APHA) was found to be 100.

For accurately determining the content of aryl alkyl sulfide in the bisphenol, the following concentration was carried out. In a 10-mL glass centrifuge container, 20 g of the bisphenol composition, 1.5 mL of ortho-xylene, and 1.0 mL of acetonitrile were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. This extraction operation was carried out 10 times, and 10 g of the obtained liquid was placed in a 100-mL flask, followed by evaporating a low-boiling component under reduced pressure. As a result, a solid was obtained. In a 10-mL glass centrifuge container, 1.5 mL of ortho-xylene and 1.0 mL of acetonitrile, as well as the obtained solid were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. After concentrating the bisphenol C composition as described above, analysis of aryl alkyl sulfide was carried out. However, since its content was less than the detection limit of 0.5 ppb by mass, no aryl alkyl sulfide could be detected.

Comparative Example 2

In a test tube for a spectroscopic color difference meter, 7.5 g of 1,1-bis(4-hydroxyphenyl)cyclohexane as a reagent and 7.5 g of diphenyl carbonate were placed, and the test tube was then placed on an aluminum block heater set to 194° C., to prepare a molten liquid. Fifteen minutes after the beginning of the heating, the molten liquid was subjected to measurement using the color difference meter. As a result, the Hazen color number (APHA) was found to be 20. The molten liquid was further heated for 2 hours, and then subjected to measurement using the color difference meter. As a result, the Hazen color number (APHA) was found to be 60.

For accurately determining the content of aryl alkyl sulfide in the bisphenol, the following concentration was carried out. In a 10-mL glass centrifuge container, 20 g of the bisphenol composition, 1.5 mL of ortho-xylene, and 1.0 mL of acetonitrile were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. This extraction operation was carried out 10 times, and 10 g of the obtained liquid was placed in a 100-mL flask, followed by evaporating a low-boiling component under reduced pressure. As a result, a solid was obtained. In a 10-mL glass centrifuge container, 1.5 mL of ortho-xylene and 1.0 mL of acetonitrile, as well as the obtained solid were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. After concentrating the bisphenol C composition as described above, analysis of aryl alkyl sulfide was carried out. However, since its content was less than the detection limit of 0.5 ppb by mass, no aryl alkyl sulfide could be detected.

For Examples 1 to 3 and Comparative Example 1, the type and the concentration of the (di)sulfide added to the bisphenol C, the Hazen color numbers of the molten liquid at Minute 15 and Hour 2, and the Hazen color number difference (Hour 2–Minute 15) of the molten liquid are summarized in Table 1. According to Table 1, it can be seen that the color tone upon the melting can be stabilized by the addition of the (di)sulfide to the bisphenol C.

For Example 4 and Comparative Example 2, the concentration of the C12SPhl added to the 1,1-bis(4-hydroxyphenyl)cyclohexane, the Hazen color numbers of the molten liquid at Minute 15 and Hour 2, and the Hazen color number difference (Hour 2–Minute 15) of the molten liquid are summarized in Table 1. According to Table 1, it can be seen that, also for the bisphenol having a 4-hydroxyphenyl group, the color tone upon the melting can be stabilized by the addition of the (di)sulfide.

high-performance liquid chromatography to analyze the amount of bisphenol C produced. As a result, the reaction yield in terms of acetone was found to be 85 mol %. Part of the organic phase was removed, and subjected to gas chromatography to analyze the amounts of didodecyl disulfide (C12SSC12) and dodecyl(4-hydroxy-3-methylphenyl)sulfide (C12SoCRS) produced. As a result, the amounts were found to be 61% by area and 24% by area, respectively (each value of % by area was calculated such that the total area of C12SSC12, C12SoCRS, and dodecanethiol was 100% by area). The organic phase was cooled from 80° C. to 30° C.,

TABLE 1

Color tone of bisphenol composition upon melting

|  | | Aryl alkyl sulfide | | Hazen color number (APHA) at Minute 15 | Hazen color number (APHA) at Hour 2 | Hazen color number difference (APHA) (Hour 2 – Minute 15) |
| --- | --- | --- | --- | --- | --- | --- |
|  | Type of bisphenol | Type | Concentration* (ppm by mass) | | | |
| Example 1 | Bisphenol C | C12SoCRS | 87 | 40 | 50 | 10 |
| Example 2 | Bisphenol C | C10SPhl | 113 | 50 | 70 | 20 |
| Example 3 | Bisphenol C | C12SPhl | 353 | 50 | 75 | 25 |
| Comparative Example 1 | Bisphenol C | None | — | 60 | 100 | 40 |
| Example 4 | 1,1-Bis(4-hydroxyphenyl)cyclohexane | C12SPhl | 1333 | 15 | 25 | 10 |
| Comparative Example 2 | 1,1-Bis(4-hydroxyphenyl)cyclohexane | None | — | 20 | 60 | 40 |

*Content with respect to bisphenol (ppm by mass)

Example 5

In a full-jacket type 1-L separable flask equipped with a thermometer, a stirrer, and a 100-mL dropping funnel, 35.0 g (1.1 mol) of methanol was placed under a nitrogen atmosphere, and then 77.7 g (0.7 mol) of 88% by mass sulfuric acid was slowly added thereto. Thereafter, 72.6 g of toluene was placed in a reactor, and 255.0 g (2.4 mol) of ortho-cresol and 7.3 g (0.04 mol) of dodecanethiol were placed in the separable flask, followed by setting the temperature in the separable flask to 50° C. In the dropping funnel, 57.0 g (1.0 mol) of acetone was placed, and it was slowly fed dropwise to the separable flask for 30 minutes. Upon completion of the dropwise addition of acetone, the reaction liquid had an orange color. The reaction liquid was reacted for 15 hours at 50° C. After completion of the reaction, 135.0 g of toluene and 175.5 g of demineralized water were fed, and the temperature was increased to 80° C. After the temperature reached 80° C., the reaction liquid was left to stand to confirm that the precipitates generated during the reaction were dissolved into the organic phase and the aqueous phase. This was followed by extraction of the aqueous phase, which corresponded to the lower phase. Thereafter, saturated sodium hydrogen carbonate solution was added to the obtained organic phase to allow neutralization, followed by confirming that the pH of the aqueous phase, which corresponded to the lower phase, became not less than 9. After extraction of the aqueous phase, which corresponded to the lower phase, demineralized water was added to the obtained organic phase, and the resulting mixture was stirred for 10 minutes. Thereafter, the mixture was left to stand, and the aqueous phase was extracted. Part of the obtained organic phase was removed, and subjected to and, when the temperature reached 30° C., 1 g of seed crystal bisphenol C was added thereto, followed by confirmation of precipitation. Thereafter, the mixture was cooled to 10° C., and, after the temperature reached 10° C., filtration was carried out under reduced pressure using a glass filter, to obtain 239.9 g of a crude bisphenol C product as a wet cake.

In a full-jacket type 1-L separable flask equipped with a thermometer and a stirrer, the whole amount of the crude bisphenol C product and 449 g of toluene were placed, and the temperature was increased to 80° C. After conforming formation of a homogeneous solution, the solution was cooled to 10° C. Thereafter, filtration was carried out under reduced pressure using a glass filter, to obtain a wet pure bisphenol C product. Using an evaporator equipped with an oil bath, a low-boiling fraction was evaporated under reduced pressure at an oil bath temperature of 100° C., to obtain 180.9 g of a bisphenol C product.

In a 10-mL glass centrifuge container, 10 g of the bisphenol C product, 1.5 mL of ortho-xylene, and 1.5 mL of acetonitrile were placed, and the resulting mixture was heated to allow complete dissolution, to provide a homogeneous solution. The solution was then allowed to cool to room temperature to obtain a solid. Thereafter, a glass filter and a receiver were arranged to the glass container to provide a centrifuge tube, and a centrifuge was used (for 10 minutes at 2000 revolutions per minute) to extract 1 g of a liquid from the solid. Part of the obtained liquid was removed, and subjected to gas chromatography to analyze the amount of dodecyl(4-hydroxy-3-methylphenyl)sulfide (C12SoCRS) contained in the liquid. As a result, the amount was found to be 0.2 ppm by mass, and no didodecyl disulfide (C12SSC12) was contained therein. From this result, the amount of C12SoCRS contained in the bisphenol C product was estimated to be about 0.02 ppm by mass with respect to the pure bisphenol C content. The C12SoCRS is a component produced by the reaction in which dodecanethiol produces bisphenol C, which component was remaining in the bisphenol C product.

In a test tube for a spectroscopic color difference meter, 15 g of the bisphenol C product was placed, and the test tube was then placed on an aluminum block heater set to 194° C., to prepare a molten liquid of the bisphenol C product. Fifteen minutes after the beginning of the heating, the molten liquid was subjected to measurement using the color difference meter. As a result, the Hazen color number (APHA) was found to be 5. The molten liquid was further heated for 2 hours, and then subjected to measurement using the color difference meter. As a result, the Hazen color number (APHA) was found to be 20.

Example 6

In a full-jacket type 1-L separable flask equipped with a thermometer, a stirrer, and a 100-mL dropping funnel, 26.2 g (mol) of methanol was placed under a nitrogen atmosphere, and then 58.5 g (0.6 mol) of 92% by mass sulfuric acid was slowly added thereto to provide a solution in which monomethyl sulfate was produced. Thereafter, 58.5 g of toluene, 192 g (1.8 mol) of ortho-cresol, and 5.5 g (0.03 mol) of dodecanethiol were added thereto, followed by setting the temperature in the separable flask to 50° C. In the dropping funnel, 71.8 g (0.7 mol) of cyclohexanone was placed, and it was slowly fed dropwise to the separable flask for 30 minutes. After completion of the dropwise addition of cyclohexanone, the reaction was allowed to proceed at 50° C. for 5 hours. After completion of the reaction, 100.0 g of ethyl acetate and 100.0 g of demineralized water were fed, and the resulting mixture was mixed. Thereafter, the mixture was left to stand, and the aqueous phase, which corresponded to the lower phase, was extracted. Thereafter, saturated sodium hydrogen carbonate solution was added to the obtained organic phase to allow neutralization, followed by confirming that the pH of the aqueous phase, which corresponded to the lower phase, became not less than 9. After extraction of the aqueous phase, which corresponded to the lower phase, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 295 ($M^+-1$) was found in the negative mode, indicating production of 1,1-bis(4-hydroxy-3-methylphenyl)cyclohexane. As a result of analysis using high-performance liquid chromatography, the amount of 1,1-bis(4-hydroxy-3-methylphenyl)cyclohexane produced was found to be 70.8% by area. Using an evaporator, the solvent was evaporated from the remaining organic phase, and recrystallization was carried out twice using toluene and acetone. By this, 90 g of a 1,1-bis(4-hydroxy-3-methylphenyl)cyclohexane product was obtained. As a result of analysis using gas chromatography, the amount of dodecyl(4-hydroxy-3-methylphenyl)sulfide (C12SoCRS) contained in the 1,1-bis(4-hydroxy-3-methylphenyl)cyclohexane product was found to be 1500 ppm by mass.

In a test tube for a spectroscopic color difference meter, 7.5 g of the 1,1-bis(4-hydroxy-3-methylphenyl)cyclohexane product and 7.5 g of diphenyl carbonate were placed, and the test tube was then placed on an aluminum block heater set to 194° C., to prepare a molten liquid. Fifteen minutes after the beginning of the heating, the molten liquid was subjected to measurement using the color difference meter. As a result, the Hazen color number (APHA) was found to be 40. The molten liquid was further heated for 2 hours, and then subjected to measurement using the color difference meter. As a result, the Hazen color number (APHA) was found to be 55.

Example 7

In a full-jacket type 1-L separable flask equipped with a thermometer, a stirrer, and a 100-mL dropping funnel, 26 g (0.8 mol) of methanol was placed under a nitrogen atmosphere, and then 58.5 g (0.5 mol) of 90% by mass sulfuric acid was slowly added thereto to provide a solution in which monomethyl sulfate was produced. Thereafter, 60 g of toluene, 197.0 g (1.8 mol) of ortho-cresol, and 5.5 g (0.03 mol) of dodecanethiol were added thereto, followed by setting the temperature in the separable flask to 50° C. Subsequently, 136 g (0.8 mol) of 9-fluorenone was placed therein, and slowly fed dropwise to the separable flask for 30 minutes. Thereafter, the reaction was allowed to proceed at 50° C. for 2 hours. After completion of the reaction, 100.0 g of ethyl acetate and 100.0 g of demineralized water were fed, and the resulting mixture was mixed. Thereafter, the mixture was left to stand, and the aqueous phase, which corresponded to the lower phase, was extracted. Thereafter, saturated sodium hydrogen carbonate solution was added to the obtained organic phase to allow neutralization, followed by confirming that the pH of the aqueous phase, which corresponded to the lower phase, became not less than 9. After extraction of the aqueous phase, which corresponded to the lower phase, demineralized water was added to the obtained organic phase, and the resulting mixture was stirred for 10 minutes. Thereafter, the mixture was left to stand, and the aqueous phase was extracted. Part of the obtained organic phase was removed and subjected to measurement by high-performance liquid chromatography. As a result, production of 9,9-bis(4-hydroxy-3-methylphenyl)fluorene was found. The amount produced was 85.6% by area. Using an evaporator, the solvent was evaporated from the remaining organic phase, and recrystallization was carried out twice using toluene and acetone. By this, 116 g of a 9,9-bis(4-hydroxy-3-methylphenyl)fluorene product was obtained. As a result of analysis using gas chromatography, the amount of dodecyl(4-hydroxy-3-methylphenyl)sulfide (C12SoCRS) contained in the 9,9-bis(4-hydroxy-3-methylphenyl)fluorene product was found to be 3000 ppm by mass.

In a test tube for a spectroscopic color difference meter, 7.5 g of the 9,9-bis(4-hydroxy-3-methylphenyl)fluorene product and 7.5 g of diphenyl carbonate were placed, and the test tube was then placed on an aluminum block heater set to 194° C., to prepare a molten liquid. Fifteen minutes after the beginning of the heating, the molten liquid was subjected to measurement using the color difference meter. As a result, the Hazen color number (APHA) was found to be 225. The molten liquid was further heated for 2 hours, and then subjected to measurement using the color difference meter. As a result, the Hazen color number (APHA) was found to be 250.

Comparative Example 3

In a test tube for a spectroscopic color difference meter, 7.5 g of 1,1-bis(4-hydroxy-3-methylphenyl)cyclohexane as a reagent and 7.5 g of diphenyl carbonate were placed, and the test tube was then placed on an aluminum block heater set to 194° C., to prepare a molten liquid. Fifteen minutes after the beginning of the heating, the molten liquid was subjected to measurement using the color difference meter. As a result, the Hazen color number (APHA) was found to be 200. The molten liquid was further heated for 2 hours, and then subjected to measurement using the color difference meter. As a result, the Hazen color number (APHA) was found to be 250.

For accurately determining the content of aryl alkyl sulfide in the bisphenol, the following concentration was carried out. In a 10-mL glass centrifuge container, 20 g of the bisphenol composition, 1.5 mL of ortho-xylene, and 1.0 mL of acetonitrile were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. This extraction operation was carried out 10 times, and 10 g of the obtained liquid was placed in a 100-mL flask, followed by evaporating a low-boiling component under reduced pressure. As a result, a solid was obtained. In a 10-mL glass centrifuge container, 1.5 mL of ortho-xylene and 1.0 mL of acetonitrile, as well as the obtained solid were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. After concentrating the bisphenol C composition as described above, analysis of aryl alkyl sulfide was carried out. However, since its content was less than the detection limit of 0.5 ppb by mass, no aryl alkyl sulfide could be detected.

Comparative Example 4

In a test tube for a spectroscopic color difference meter, 7.5 g of 9,9-bis(4-hydroxy-3-methylphenyl)fluorene as a reagent and 7.5 g of diphenyl carbonate were placed, and the test tube was then placed on an aluminum block heater set to 194° C., to prepare a molten liquid. Fifteen minutes after the beginning of the heating, the molten liquid was subjected to measurement using the color difference meter. As a result, the Hazen color number (APHA) was found to be 500, which is the upper limit o the measurement device. Since the value reached the upper limit, measurement of the Hazen color number by further heating was not carried out.

For accurately determining the content of aryl alkyl sulfide in the bisphenol, the following concentration was carried out. In a 10-mL glass centrifuge container, 20 g of the bisphenol composition, 1.5 mL of ortho-xylene, and 1.0 mL of acetonitrile were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. This extraction operation was carried out 10 times, and 10 g of the obtained liquid was placed in a 100-mL flask, followed by evaporating a low-boiling component under reduced pressure. As a result, a solid was obtained. In a 10-mL glass centrifuge container, 1.5 mL of ortho-xylene and 1.0 mL of acetonitrile, as well as the obtained solid were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. After concentrating the bisphenol C composition as described above, analysis of aryl alkyl sulfide was carried out. However, since its content was less than the detection limit of 0.5 ppb by mass, no aryl alkyl sulfide could be detected.

For Examples 5 to 7 and Comparative Examples 1, 3, and 4, the concentration of C12SoCRS contained in the bisphenol product, the Hazen color numbers of the molten liquid at Minute 15 and Hour 2, and the Hazen color number difference (Hour 2–Minute 15) of the molten liquid are summarized in Table 2. According to Table 2, it can be seen that the color tone upon the melting can be stabilized by producing a (di)sulfide in the reaction for producing a bisphenol, and including the (di)sulfide in the bisphenol product.

TABLE 2

Color tone of bisphenol upon melting

|  | Bisphenol Preparation method | Type of bisphenol | C12SoCRS Concentration* (ppm by mass) | Hazen color number (APHA) at Minute 15 | Hazen color number (APHA) at Hour 2 | Hazen color number difference (APHA) (Hour 2 – Minute 15) |
|---|---|---|---|---|---|---|
| Example 5 | Sulfuric acid MET method | Bisphenol C | 0.02 | 5 | 20 | 15 |
| Example 6 | Sulfuric acid MET method | 1,1-Bis (4-hydroxy-3-methylphenyl) cyclohexane | 1500 | 40 | 55 | 15 |
| Example 7 | Sulfuric acid MET method | 9,9-Bis (4-hydroxy-3-methylphenyl) fluorene | 3000 | 225 | 250 | 25 |

TABLE 2-continued

Color tone of bisphenol upon melting

| | Bisphenol Preparation method | Type of bisphenol | C12SoCRS Concentration* (ppm by mass) | Hazen color number (APHA) at Minute 15 | Hazen color number (APHA) at Hour 2 | Hazen color number difference (APHA) (Hour 2 − Minute 15) |
|---|---|---|---|---|---|---|
| Comparative Example 1 | Reagent | Bisphenol C | None | 60 | 100 | 40 |
| Comparative Example 3 | Reagent | 1,1-Bis (4-hydroxy-3-methylphenyl) cyclohexane | None | 200 | 250 | 50 |
| Comparative Example 4 | Reagent | 9,9-Bis (4-hydroxy-3-methylphenyl) fluorene | None | 500 (upper limit value) | — | — |

*Content with respect to bisphenol (ppm by mass)

Example 8

In a full-jacket type 1-L separable flask equipped with a thermometer, a stirrer, and a 100-mL dropping funnel, 35.0 g (1.1 mol) of methanol was placed under a nitrogen atmosphere, and then 79.2 g (0.7 mol) of 88% by mass sulfuric acid was slowly added thereto. Thereafter, 72.6 g of toluene was placed in a reactor, and 255.0 g (2.4 mol) of ortho-cresol and 7.3 g (0.04 mol) of dodecanethiol were placed in the separable flask, followed by setting the temperature in the separable flask to 50° C. In the dropping funnel, 57.0 g (1.0 mol) of acetone was placed, and it was slowly fed dropwise to the separable flask for 30 minutes. Upon completion of the dropwise addition of acetone, the reaction liquid had a brown color. The reaction liquid was reacted for 15 hours at 50° C. After completion of the reaction, 135.0 g of toluene and 175.5 g of demineralized water were fed, and the temperature was increased to 80° C. After the temperature reached 80° C., the reaction liquid was left to stand to confirm that the precipitates generated during the reaction were dissolved into the organic phase and the aqueous phase. This was followed by extraction of the aqueous phase, which corresponded to the lower phase. Thereafter, saturated sodium hydrogen carbonate solution was added to the obtained organic phase to allow neutralization, followed by confirming that the pH of the aqueous phase, which corresponded to the lower phase, became not less than 9. After extraction of the aqueous phase, which corresponded to the lower phase, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 87 mol %. Part of the organic phase was removed, and subjected to gas chromatography to analyze the amounts of didodecyl disulfide (C12SSC12) and dodecyl(4-hydroxy-3-methylphenyl)sulfide (C12SoCRS) produced. As a result, the amounts were found to be 61% by area and 24% by area, respectively (each value of % by area was calculated such that the total area of C12SSC12, C12SoCRS, and dodecanethiol was 100% by area). The organic phase was cooled from 80° C. to 30° C., and, when the temperature reached 30° C., 1 g of seed crystal bisphenol C was added thereto, followed by confirmation of precipitation. Thereafter, the mixture was cooled to 10° C., and, after the temperature reached 10° C., filtration was carried out using a centrifuge (for 10 minutes at 2500 revolutions per minute), to obtain 241.2 g of a crude bisphenol C product as a wet cake.

In a full-jacket type 1-L separable flask equipped with a thermometer and a stirrer, the whole amount of the crude bisphenol C product and 449 g of toluene were placed, and the temperature was increased to 80° C. After conforming formation of a homogeneous solution, the solution was cooled to 10° C. Thereafter, filtration was carried out using a centrifuge (for 10 minutes at 2500 revolutions per minute) to obtain a wet pure bisphenol C product. Using an evaporator equipped with an oil bath, a low-boiling fraction was evaporated under reduced pressure at an oil bath temperature of 100° C., to obtain 190.1 g of a bisphenol C product.

In a 10-mL glass centrifuge container, 20 g of the bisphenol C composition, 1.5 mL of ortho-xylene, and 1 mL of acetonitrile were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. This extraction operation was carried out 10 times, and 10 g of the obtained liquid was placed in a 100-mL flask, followed by evaporating a low-boiling component under reduced pressure. As a result, a solid was obtained. In a 10-mL glass centrifuge container, 1.5 mL of ortho-xylene and 1 mL of acetonitrile, as well as the obtained solid were placed, and the resulting mixture was heated to allow complete dissolution, to provide a homogeneous solution. The obtained solution was allowed to cool to room temperature to obtain a solid. Thereafter, a glass filter and a receiver were arranged to provide a centrifuge tube, and a centrifuge was used (for 10 minutes at 2000 revolutions per minute) to extract 1 g of a liquid from the solid. After concentrating the bisphenol C composition as described above, analysis of aryl alkyl sulfide (C12SoCRS) was carried out. As a result, it was detected at 0.2 ppm by mass. From this result, the amount of the C12SoCRS contained in the bisphenol C product was estimated to be about 1 ppb by mass with respect to the pure bisphenol C content. The C12SoCRS is a component produced by the reaction in which dodecanethiol produces bisphenol C, which component was remaining in the bisphenol C product.

In a test tube for a spectroscopic color difference meter, 15 g of the bisphenol C product was placed, and the test tube was then placed on an aluminum block heater set to 194° C., to prepare a molten liquid of the bisphenol C product. Fifteen minutes after the beginning of the heating, the molten liquid was subjected to measurement using the color difference meter. As a result, the Hazen color number (APHA) was found to be 5. The molten liquid was further heated for 2 hours, and then subjected to measurement using the color difference meter. As a result, the Hazen color number (APHA) was found to be 20. That is, the Hazen color number difference (APHA) (Hour 2–Minute 15) was 15.

What is claimed is:

1. A bisphenol composition comprising an aryl alkyl sulfide at 1 ppb by mass to 1% by mass with respect to a bisphenol, wherein the content of the bisphenol is not less than 95.0% by mass.

2. The bisphenol composition according to claim 1, wherein the aryl alkyl sulfide contains an aryl group which is a hydroxyphenyl group, a hydroxytolyl group, or a hydroxyxylyl group.

3. The bisphenol comosition according to claim 1, wherein the aryl alkyl sulfide contains a C8-C30 alky l goup.

4. The bisphenol composition according to claim 1, wherein the content of the bisphenol is not less than 97.0% by mass.

5. A method of producing a bisphenol composition, comprising producing a monoalkyl sulfate catalyst by reacting sulfuric acid and an aliphatic alcohol and subsequently reacting a ketone or an aldehyde with an aromatic alcohol in the presence of the monoalkyl sulfite catalyst and an alkylthiol catalyst to produce the bisphenol composition according to claim 1,
wherein a concentration of the sulfuric acid is 80 to 95% by mass.

6. A method of producing a polycarbonate resin, comprising reacting the bisphenol composition according to claim 1 in the presence of an alkali metal compound and/or an alkaline earth metal compound to produce a polycarhonate resin.

7. A bisphenol composition comprising a dialkyl disulfide at 1 ppb by mass to 1% by mass with respect to a bisphenol, wherein the content of the bisphenol is not less than 95.0% by mass.

8. The bisphenol composition according to claim 7, wherein the dialkyl disulfide contains a C8-C30 alkyl group.

9. The bisphenol composition according to claim 7, wherein the content of the bisphenol is not less than 97.0% by mass.

10. A method of producing a bisphenol composition, comprising producing a monoalkyl sulfite catalyst by reacting sulfuric acid and an aliphatic alcohol and subsequently reacting a ketone or an aldehyde with an aromatic alcohol in the presence of a monoalkyl sulfate catalyst and an alkylthiol catalyst to produce the bisphenol composition according to claim 7,
wherein a concentration of the sulfuric acid is 80 to 95% by mass.

11. A method of producing a polycarbonate resin, comprising reacting the bisphenol composition according to claim 7 in the presence of an alkali metal compound and/or an alkaline earth metal compound to produce a polycarbonate resin.

12. A polycarbonate resin comprising aryl alkyl sulfide structural units at not less than 1 ppb by glass with respect to bisphenol structural units.

\* \* \* \* \*